United States Patent
Koga et al.

(10) Patent No.: US 11,883,617 B2
(45) Date of Patent: Jan. 30, 2024

(54) BALLOON CATHETER AND METHOD FOR PRODUCING SAME

(71) Applicant: KANEKA CORPORATION, Osaka (JP)

(72) Inventors: Yojiro Koga, Osaka (JP); Noriko Wadahama, Osaka (JP)

(73) Assignee: KANEKA CORPORATION, Osaka (JP)

( * ) Notice: Subject to any disclaimer, the term of this patent is extended or adjusted under 35 U.S.C. 154(b) by 801 days.

(21) Appl. No.: 16/767,553

(22) PCT Filed: Nov. 19, 2018

(86) PCT No.: PCT/JP2018/042693
§ 371 (c)(1),
(2) Date: May 27, 2020

(87) PCT Pub. No.: WO2019/107206
PCT Pub. Date: Jun. 6, 2019

(65) Prior Publication Data
US 2021/0170147 A1    Jun. 10, 2021

(30) Foreign Application Priority Data

Nov. 30, 2017    (JP) .................................. 2017-230943

(51) Int. Cl.
*A61M 25/10*    (2013.01)
*A61B 17/3207*    (2006.01)

(52) U.S. Cl.
CPC .... *A61M 25/1002* (2013.01); *A61M 25/1029* (2013.01); *A61B 17/3207* (2013.01);
(Continued)

(58) Field of Classification Search
CPC .......... A61M 25/1002; A61M 25/1036; A61M 2025/1086; A61M 2025/1004;
(Continued)

(56) References Cited

U.S. PATENT DOCUMENTS 8,192,675 B2 *    6/2012 Burton ........... A61B 17/320725
264/514
2003/0153870 A1    8/2003 Meyer et al.
(Continued)

FOREIGN PATENT DOCUMENTS

JP    2005517474 A    6/2005
JP    2007135880 A    6/2007
(Continued)

OTHER PUBLICATIONS

International Search Report issued in corresponding International Application No. PCT/JP2018/042693; dated Feb. 19, 2019 (1 page).
(Continued)

*Primary Examiner* — Nathan R Price
*Assistant Examiner* — Tania Ismail
(74) *Attorney, Agent, or Firm* — Osha Bergman Watanabe & Burton LLP

(57) ABSTRACT

A balloon catheter may include a shaft having a distal side and a proximal side and a balloon provided at the distal side of the shaft. The balloon may have a plurality of wings in a deflated state, with each of the wings having a projection on an outer surface in a wrapped state, and each of the projections having a projecting direction, which is opposite to a wrapping direction of the wing. In a cross section that is perpendicular to a long axis direction of the balloon, a base of the projection may have a base first end part farther from a tip of the wing and a base second end part closer to the tip of the wing, and a tip of the projection may be closer to a base of the wing with respect to a line passing through the base first end part which is perpendicular to a line passing through the base first end part and the base second end part.

17 Claims, 10 Drawing Sheets

(52) U.S. Cl.
CPC .. *A61B 17/320725* (2013.01); *A61M 25/1036* (2013.01); *A61M 2025/1004* (2013.01); *A61M 2025/109* (2013.01); *A61M 2025/1079* (2013.01); *A61M 2025/1086* (2013.01)

(58) Field of Classification Search
CPC ......... A61M 2025/109; A61B 17/3207; A61B 17/320725
See application file for complete search history.

(56) References Cited

U.S. PATENT DOCUMENTS

| | | |
|---|---|---|
| 2006/0184191 A1* | 8/2006 | O'Brien ......... A61B 17/320725 606/192 |
| 2009/0234283 A1 | 9/2009 | Burton et al. |
| 2012/0215251 A1 | 8/2012 | Burton et al. |
| 2014/0088624 A1 | 3/2014 | Burton et al. |
| 2016/0095619 A1 | 4/2016 | McMahon et al. |
| 2017/0112526 A1 | 4/2017 | Burton et al. |
| 2018/0296241 A1 | 10/2018 | Burton et al. |

FOREIGN PATENT DOCUMENTS

| | | |
|---|---|---|
| JP | 2011513031 A | 4/2011 |
| JP | 2016521169 A | 7/2016 |

OTHER PUBLICATIONS

Written Opinion of the International Searching Authority issued in corresponding International Application No. PCT/JP2018/042693; dated Feb. 19, 2019 (4 pages).

* cited by examiner

[FIG. 1]
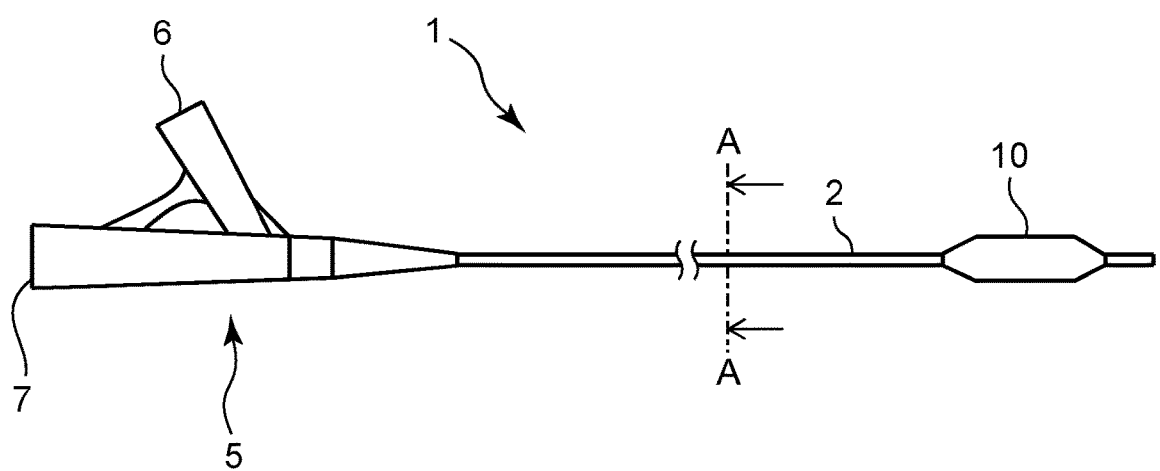

[FIG. 2]
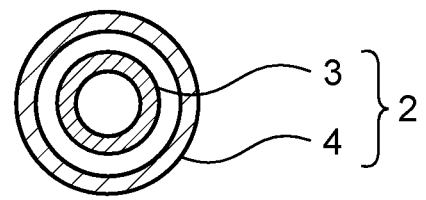

[FIG. 3]
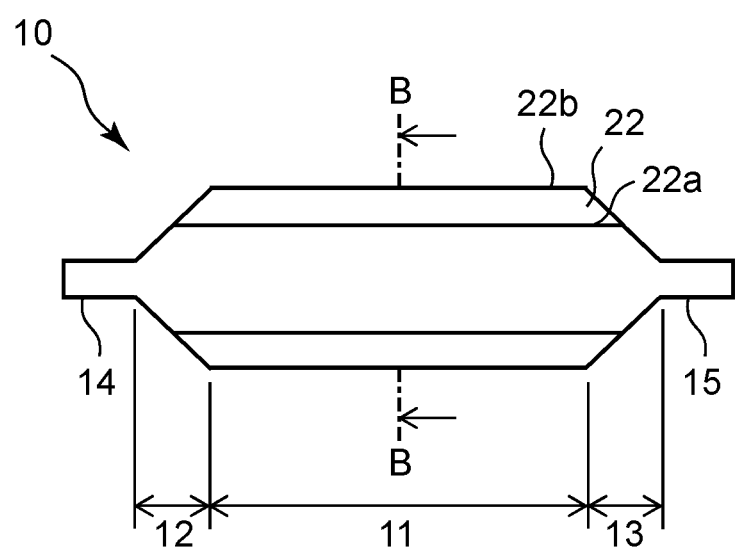

[FIG. 4]
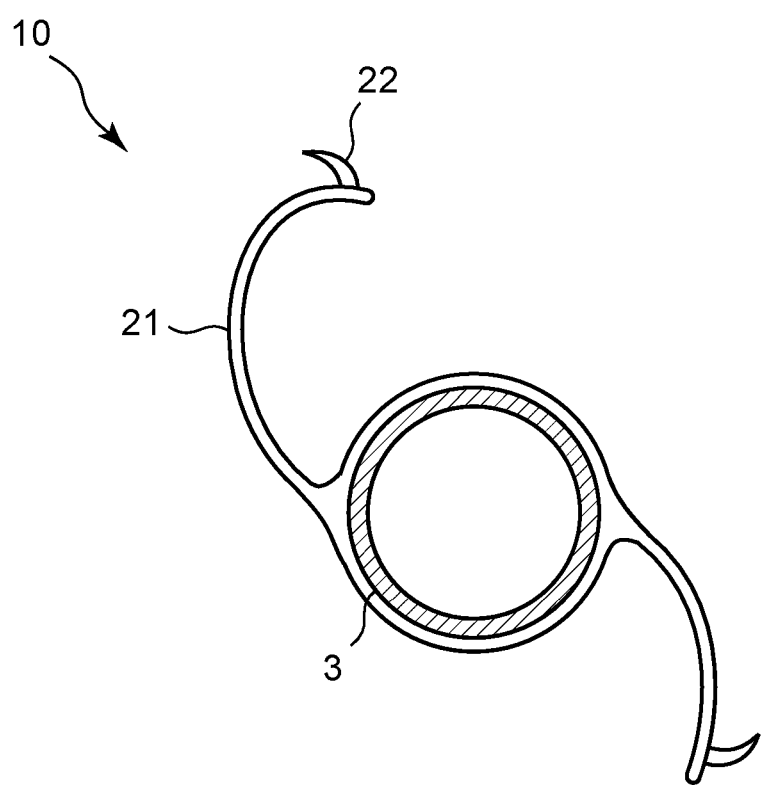

[FIG. 5]
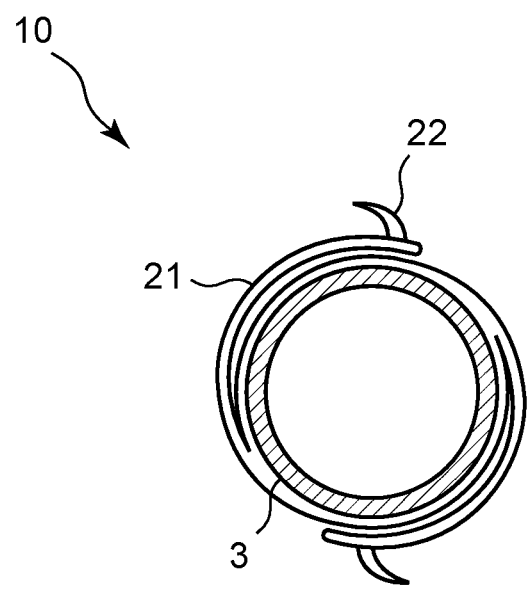

[FIG. 6]
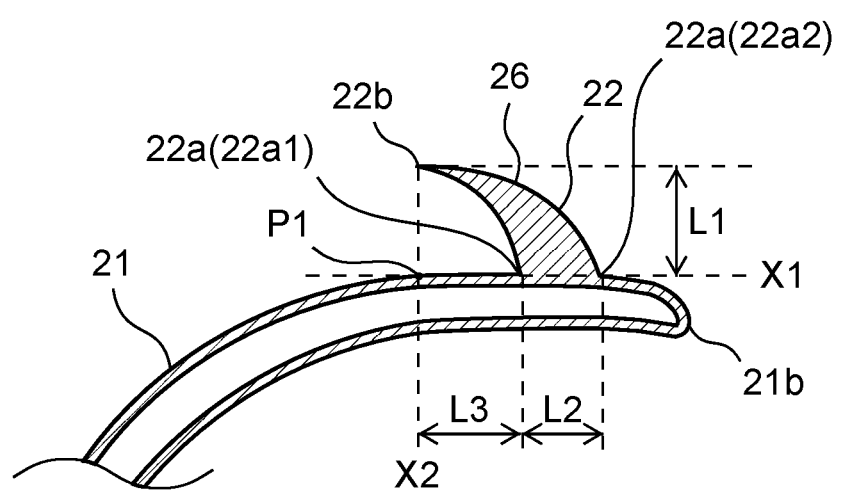

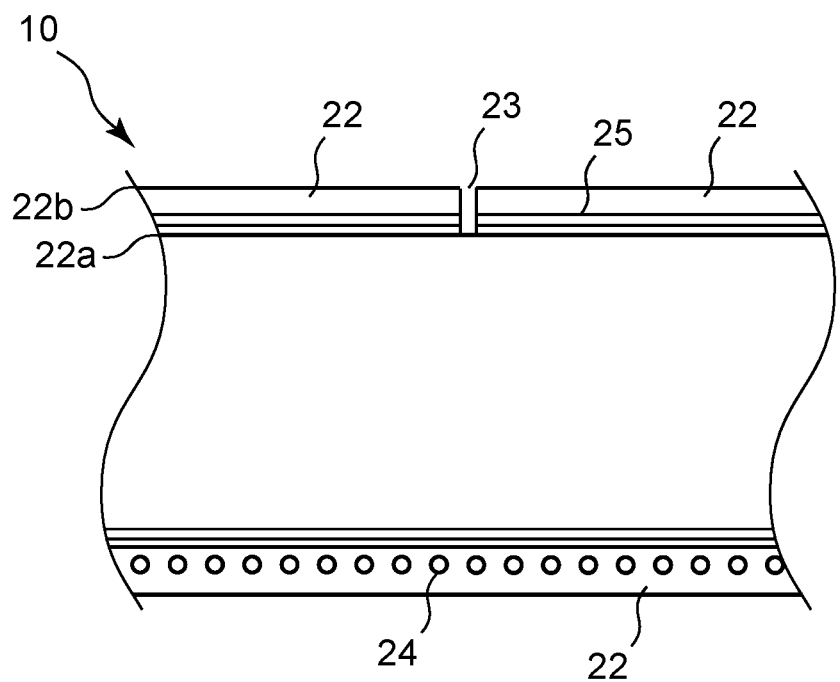
[FIG. 7]

[FIG. 8]
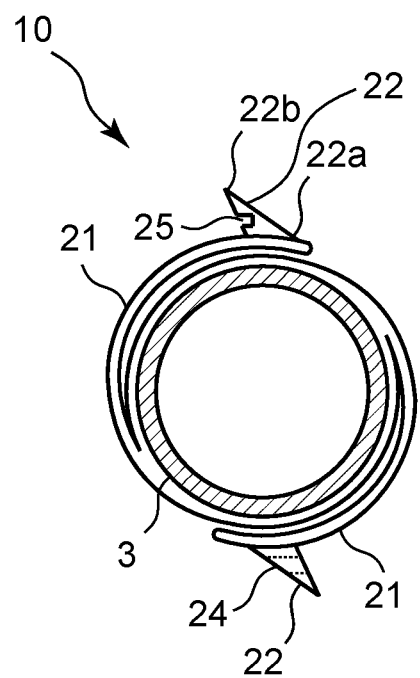

[FIG. 9]
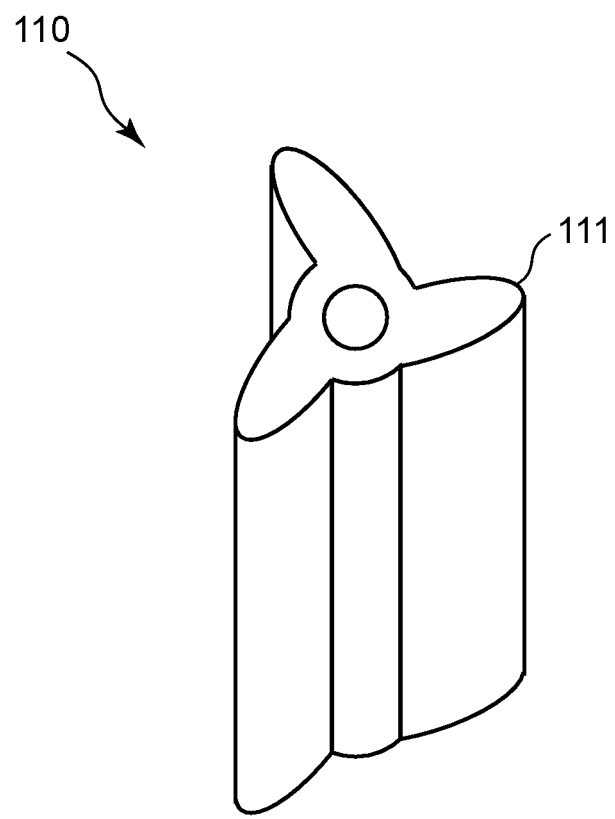

[FIG. 10]
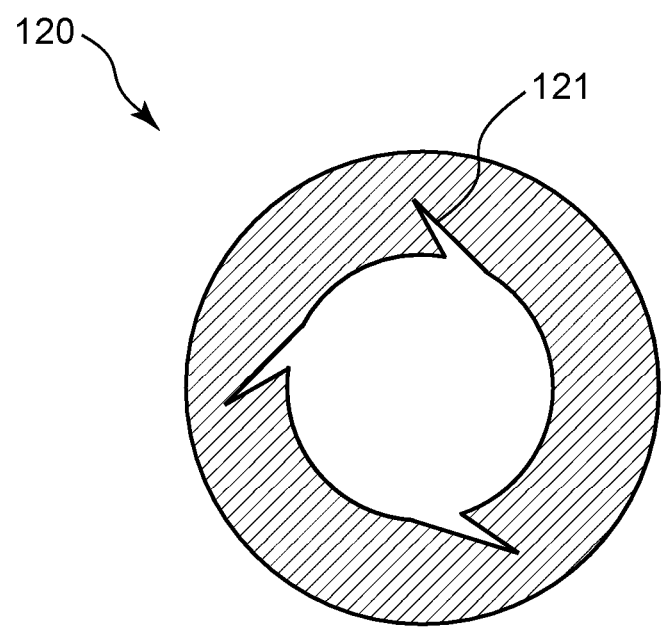

BALLOON CATHETER AND METHOD FOR PRODUCING SAME

TECHNICAL FIELD

One or more embodiments of the present disclosure relate to a balloon catheter in which a balloon has a projecting portion.

BACKGROUND

It has been known that various diseases are caused by stagnant circulation of blood due to constriction of a blood vessel which is a flow path through which blood is circulated in the body. Particularly when a coronary artery supplying blood to the heart becomes stenosed, serious diseases such as angina or myocardial infarction may be caused. As one of methods for treating such a stenosed part of a blood vessel, technique (for example, angioplasty such as PTA or PTCA) has been used for dilating the stenosed part using a balloon catheter. Angioplasty is a minimally invasive therapy that does not require thoracotomy, such as bypass surgery, and thus is widely used.

A stenosed part sclerosed by calcification or the like may occur on the inner wall of a blood vessel. In such a calcified lesion, it is difficult to dilate the sclerosed stenosed part with a common balloon catheter.

A method has been used of dilating a stenosed part of a blood vessel by placing an indwelling dilator called a stent in the stenosed part. However, ISR (In-Stent-Restenosis) lesions may occur in which stenosis occurs again in the blood vessel due to excessive neointimal proliferation in the blood vessel after the treatment. In the ISR lesion, the neointima is soft and has a smooth surface. Therefore, when a common balloon catheter is used, the position of the balloon may be displaced from the lesion during inflation of the balloon, so that the blood vessel may be damaged.

As balloon catheters that can dilate stenosed parts caused by the calcified lesion or the ISR lesion as described above, there are balloon catheters provided with protrusions on the outer peripheral surface of the balloon (for example, Patent Documents 1 to 4).

PATENT DOCUMENTS

Patent Document 1: JP-A-2011-513031
Patent Document 2: JP-A-2005-517474
Patent Document 3: JP-A-2016-521169
Patent Document 4: JP-A-2007-135880

However, the balloon catheters having protrusions as disclosed in Patent Documents 1 to 4 have poor passage within a blood vessel, because the protrusions protrude radially outward from the central axis of the catheter. Further, depending on the state of the calcified lesion or the ISR lesion, even the balloon catheters as disclosed in Patent Documents 1 to 4 cannot sufficiently dilate the stenosed part.

SUMMARY

One or more embodiments of the present disclosure has been made in view of the above-described circumstances, and the object thereof is to provide a balloon catheter that has excellent passage within a blood vessel and can sufficiently dilate the stenosed part by applying strong stress on the stenosed part.

A balloon catheter of one or more embodiments of the present invention comprises: a shaft having a distal side and a proximal side; and a balloon provided at the distal side of the shaft, wherein the balloon has a plurality of wings in a deflated state, each wing has a projecting portion on an outer surface in a wrapping state, a projecting direction of which is opposite to the wrapping direction of the wing, in cross section perpendicular to a long axis direction of the balloon, a base of the projecting portion has a base first end part farther from a tip of the wing and a base second end part closer to the tip of the wing, and a tip of the projecting portion is closer to a base of the wing respect to a line passing through the base first end part which is perpendicular to a line passing through the base first end part and the base second end part.

In one or more embodiments, the balloon catheter is provided wherein, in a cross section perpendicular to a long axis direction of the balloon, a linear component passing through the base first end part and the base second end part in a vector from the base first end part of the projecting portion toward the tip of the wing having the projecting portion, and a linear component passing through the base first end part and the base second end part in a vector from the base first end part of the projecting portion toward the tip of the projecting portion are opposite.

In one or more embodiments, the balloon catheter is provided wherein the projecting portion is exposed when the wings are wrapping.

In one or more embodiments, the balloon catheter is provided wherein a number of the wings is at least two, and a number of the projecting portion is two or more and five or less.

In one or more embodiments, the balloon catheter is provided wherein a number of the projecting portion provided on each of the plurality of wings is at least one.

In one or more embodiments, the balloon catheter is provided wherein the projecting portion is at least partially provided with a discontinuous part in a distal and proximal direction of the shaft.

In one or more embodiments, the balloon catheter is provided wherein the projecting portion is formed with a plurality of holes aligned in a distal and proximal direction of the shaft.

In one or more embodiments, the balloon catheter is provided wherein the projecting portion is formed with a recess extending along a distal and proximal direction of the shaft.

In one or more embodiments, the balloon catheter is provided wherein, in a cross section perpendicular to the long axis direction of the balloon, a height from straight line passing through the base first end part and the base second end part to a tip of the projecting portion is greater than a distance from the base first end part to the base second end.

In one or more embodiments, the balloon catheter is provided wherein, in a cross section perpendicular to the long axis direction of the balloon, a height from a straight line passing through the base first end part and the base second end part to a tip part of the projecting portion is less than a distance from the base first end part to the base second end part.

In one or more embodiments, the balloon catheter is provided wherein, in a cross section perpendicular to the long axis direction of the balloon, the projecting portion has an arc at least at a part from the base first end part to the tip of the projecting portion and at least at a part from the base second end part to the tip of the projecting portion.

In one or more embodiments, the balloon catheter provided wherein, in a cross section perpendicular to the long axis direction of the balloon, a distance from a point of intersection where a perpendicular line from the tip of the projecting portion to a straight line passing through the base first end part and the base second end part contacts a straight line passing through the base first end part and the base second end part to the base first end part is greater than a distance from the base first end part to the base second end part.

In one or more embodiments, the balloon catheter is provided wherein a material constituting the projecting portion is same as a material constituting the wings.

A method for manufacturing a balloon catheter of one or more embodiments of the present disclosure comprises preparing a resin block having a plurality of protrusions in a cross section perpendicular to a long axis direction, protruding directions of the plurality of protrusions having a one-circumferential-direction component; preparing a hollow mold; and placing the resin block inside the mold.

In one or more embodiments, the method for manufacturing a balloon catheter is provided wherein the mold has a recessed part in which the protrusions are placeable.

The balloon catheter according to one or more embodiments of the present disclosure has a projecting portion on an outer surface of each wing of a balloon in a wrapping state of the wing, wherein a projecting direction of which is opposite to the wrapping direction of the wing. Thus, the balloon catheter has excellent passage within a blood vessel. Further, the balloon easily catches on the stenosed part, and a strong stress can be applied to the stenosed part, whereby the stenosed part can be sufficiently dilated.

BRIEF DESCRIPTION OF THE DRAWINGS

FIG. 1 is a side view of a balloon catheter according to one or more embodiments of the present disclosure.

FIG. 2 is a sectional view of one or more embodiments of the balloon catheter shown in FIG. 1 along a line II-II.

FIG. 3 is an enlarged view of a balloon included in a balloon catheter according to one or more embodiments of the present disclosure.

FIG. 4 shows a deflated state of the balloon shown in FIG. 3 along a line IV-IV.

FIG. 5 shows a wrapping state of the balloon shown in FIG. 4.

FIG. 6 is an enlarged view of a projecting portion of a balloon according to one or more embodiments of the present disclosure.

FIG. 7 is a side view showing another example of a balloon according to one or more embodiments of the present disclosure.

FIG. 8 is a sectional view showing another example of a balloon according to one or more embodiments of the present disclosure.

FIG. 9 is a perspective view of a resin block according to the one or more embodiments of the present disclosure.

FIG. 10 is a sectional view of a cavity shape of a mold according to one or more embodiments of the present disclosure.

DETAILED DESCRIPTION

One or more embodiments of the present disclosure will be described below in more detail by way of the following embodiments. However, one or more embodiments of the present disclosure is not limited to the following embodiments. It is obvious that the present invention can be carried out by making modifications, as appropriate, in accordance with the gist described above or later, and such modifications are also included in the technical scope of the present disclosure. Note that, in each drawing, hatching, reference signs for components, and the like may be omitted for convenience of description, and in such a case, the specification and other drawings are to be referred to. Further, the dimensions of the various components in the drawings are not limited to provide for the purpose of facilitating the understanding of the feature of one or more embodiments of the present disclosure, and the dimensions may differ from the actual dimensions in some cases.

An overall configuration of a balloon catheter according to one or more embodiments of the present disclosure will be described with reference to FIGS. 1 to 3. FIG. 1 shows a configuration example of a so-called over-the-wire balloon catheter in which a wire is inserted from a distal side to a proximal side of a shaft. One or more embodiments of the present disclosure is also applicable to a so-called rapid exchange balloon catheter in which a wire is inserted from the distal side to a position at the middle between the distal side and the proximal side of the shaft.

The balloon catheter 1 has a shaft 2 having a distal side and a proximal side, and a balloon 10 provided on the distal side of the shaft 2. A hub 5 is provided on the proximal side of the shaft 2.

In one or more embodiments of the present disclosure, the proximal side refers to a user side with respect to the extending direction of the shaft 2, and the distal side refers to a side opposite to the proximal side, that is, a treatment target side. Further, the extending direction of the shaft 2 is referred to as a long axis direction. The radial direction refers to the radial direction of the shaft 2, the inner side in the radial direction refers to the direction toward the center of the axis of the shaft 2, and the outer side in the radial direction refers to the direction toward the opposite side to the inner side.

The balloon catheter 1 is configured such that fluid is supplied from the hub 5 to the inside of the balloon 10 through the shaft 2, and can control inflation and deflation of the balloon 10 using an indeflator (balloon pressurizer). The fluid may be a pressure fluid pressurized by a pump or the like.

Commonly, the shaft 2 is internally provided with a fluid flow path and a guide wire insertion path for a guide wire that guides the movement of the shaft 2. For example, the shaft 2 has an inner tube 3 and an outer tube 4, wherein the inner tube 3 functions as the insertion path for the guide wire, and a space between the inner tube 3 and the outer tube 4 functions as the fluid flow path. In this case, on the distal side of the shaft 2, the inner tube 3 extends from the distal end of the outer tube 4 and penetrates the balloon 10 in the axial direction. Thus, the distal side of the balloon 10 is connected to the inner tube 3 and the proximal side of the balloon 10 is connected to the outer tube 4.

The hub 5 includes a fluid injection portion 6 that communicates with the flow path of the pressure fluid, and a guide wire insertion portion 7 that communicates with the insertion path for the guide wire. The guide wire insertion portion 7 having a function of inserting the guide wire there through can also function as an injection port for drug or the like and as a suction port for fluid or the like in a body cavity.

The balloon 10, the shaft 2 (inner tube 3 and outer tube 4), and the hub 5 can be joined by using conventionally known joining methods such as a method using an adhesive or heat welding. A radiopaque marker may be placed in the portion of the shaft 2 where the balloon 10 is located in order that an operator can confirm the position of the balloon 10 under X-ray fluoroscopy.

In one or more embodiments, the balloon 10 may have a straight tube portion 11 as shown in FIG. 3. When the balloon 10 is configured as described above, the contact area between the balloon 10 and the stenosed part can be increased, whereby the stenosed part can be easily dilated. In one or more embodiments, the balloon 10 may have a proximal tapered portion 12 connected to the proximal side of the straight tube portion 11, and a distal tapered portion 13 connected to the distal side of the straight tube portion 11, the proximal tapered portion 12 and the distal tapered portion 13 being reduced in diameter with distance from the straight tube portion 11. Due to such configuration of the balloon 10, the strength of the balloon 10 can be increased. In addition, a step generated when the balloon 10 is wrapped around the shaft 2 can be reduced, whereby the balloon 10 can be easily inserted into a blood vessel. In order to fix the balloon 10, a cylindrical proximal sleeve 14 may be connected to the proximal side of the proximal tapered portion 12, and a cylindrical distal sleeve 15 may be connected to the distal side of the distal tapered portion 13. In the balloon catheter 1 shown in FIG. 1, the proximal sleeve 14 is joined to the outer tube 4 of the shaft 2, and the distal sleeve 15 is joined to the inner tube 3 of the shaft 2. The balloon 10 can be configured such that the distal tapered portion 13 is inflated by a fluid supplied from the proximal tapered portion 12 through the straight tube portion 11. In one or more embodiments of the present disclosure, an inflatable part is regarded as the balloon 10.

Examples of the material constituting the balloon 10 include: polyolefin resins such as polyethylene, polypropylene, and ethylene-propylene copolymers; polyester resins such as polyethylene terephthalate and polyester elastomers; polyurethane resins such as polyurethane and polyurethane elastomers; polyphenylene sulfide resins; polyamide resins such as polyamide or polyamide elastomers; fluorine resins; silicon resins; and natural rubber such as latex rubber. These materials may be used alone, or two or more of them may be used in combination. Among them, polyamide resin, polyester resin, and polyurethane resin may be used. Particularly, an elastomer resin may be used from the viewpoint of reduction in thickness and flexibility of the balloon. Among polyamide resins, nylon 11 and nylon 12, for example, can be used as materials suitable for the balloon 10, and nylon 12 is suitably used because it can be relatively easily molded during blow molding. From the viewpoint of reduction in thickness and flexibility of the balloon 10, a polyamide elastomer, such as a polyether ester amide elastomer or a polyamide ether elastomer, may be used. Among them, a polyether ester amide elastomer may be used from the viewpoint of high yield strength and high dimensional stability of the balloon 10.

In one or more embodiments, the outer diameter of the balloon 10 may be 0.5 mm or more, 1 mm or more, or 3 mm or more. Due to the lower limit value of the outer diameter of the balloon 10 being set as described above, the stenosed part in the blood vessel can be sufficiently dilated. Further, in one or more embodiments the outer diameter of the balloon 10 may be 35 mm or less, 30 mm or less, or 25 mm or less. Due to the upper limit value of the outer diameter of the balloon 10 being set as described above, a sufficient blood flow path can be ensured in a blood vessel.

In one or more embodiments, the length of the balloon 10 in the long axis direction may be 5 mm or more, 10 mm or more, or 15 mm or more. Due to the lower limit value of the length of the balloon 10 in the long axis direction being set as described above, the area of the stenosed part that can be dilated at a time can be increased. In addition, in one or more embodiments the length of the balloon 10 in the long axis direction may be 300 mm or less, 200 mm or less, or 100 mm or less. Due to the upper limit value of the length of the balloon 10 in the long axis direction being set as described above, a load during inflation of the balloon 10 can be reduced.

In one or more embodiments, the thickness of the balloon 10 may be 5 μm or more, 7 μm or more, or 10 μm or more. Due to the lower limit value of the thickness of the balloon 10 being set as described above, sufficient strength of the balloon 10 can be obtained. In one or more embodiments, the thickness of the balloon 10 may be 45 μm or less. The thickness of the balloon 10 can be set according to the purpose of use of the balloon catheter. For example, when used as a high pressure resistant balloon, the balloon 10 may have a thickness of 30 μm or more and 45 μm or less in one or more embodiments. Moreover, when it is desired to improve the passage of the balloon portion, the thickness may be set to 30 μm or less in one or more embodiments.

As shown in FIG. 4, the balloon 10 of one or more embodiments has a plurality of wings 21 in a deflated state. The wing 21 refer to portions where the inner surfaces of the balloon 10 are partly in contact with each other when the balloon 10 is deflated.

In one or more embodiments, the number of the wing 21 may be one or more, and may be at least two or three. Due to such configuration of the wings 21, the balloon 10 is easily folded when being deflated. Each wing 21 may have a discontinuous part 23, which will be described later, in distal and proximal direction of the shaft 2. Even if the wing 21 has the discontinuous part 23 in the distal and proximal direction of the shaft 2, such wing 21 is regarded as a single piece.

As shown in FIG. 5, each wing 21 has a projecting portion 22 on an outer surface in a wrapping state. The wrapping state of the wing 21 refers to a state in which the wing 21 is folded while being wrapped along the outer periphery of the balloon 10 in the deflated state of the balloon 10.

The projecting direction of the projecting portion 22 has a component in the direction opposite to the wrapping direction of the wing 21. In other words, the projecting direction of the projecting portion 22 of which is opposite to the wrapping direction of the wing 21. That is, as shown in FIG. 6, the projecting portion 22 is configured such that an angle between a straight line connecting a base 22a of the projecting portion 22 and a tip 22b of the projecting portion 22 and a straight line connecting the base 22a of the projecting portion 22 and a tip 21b of the wing 21 exceeds 90 degrees. Due to such configuration of the projecting portion 22, when the balloon 10 passes through a blood vessel, the projecting portion 22 is less likely to catch on the inner wall of the blood vessel, whereby passage of the balloon 10 within the blood vessel can be improved. Further, when the balloon 10 is inserted while being rotated in the direction from the tip 22b of the projecting portion 22 toward the tip 21b of the wing 21 during passage of the balloon 10 through the blood vessel, interference between the projecting portion 22 and the inner wall of the blood vessel can be prevented, whereby the passage of the balloon 10 within the blood vessel can be further improved.

In a cross section perpendicular to a long axis direction of the balloon 10, the base 22a of the projecting portion 22 has a base first end part 22a1 farther from the tip 21b of the wing 21 and a base second end part 22a2 closer to the tip 21b of the wing 21, and the tip 22b of projecting portion 22 is perpendicular to a straight line X1 passing through the base first end part 22a1 and the base second end part 22a2, and is closer to the base of the wing 21 than a straight line passing through the base first end part 22a1. In other words, a tip 22b of the projecting portion 22 is closer to a base of the wing 21 respect to a line passing through the base first end part 22a1 which is perpendicular to a line X1 passing through the base first end part 22a1 and the base second end part 22a2. Due to such configuration of the projecting portion 22, passage of the balloon 10 within the blood vessel can be improved.

Examples of the material constituting the projecting portion 22 include: metal such as stainless steel, aluminum, aluminum alloy, titanium, titanium alloy, copper, copper alloy, tantalum, or cobalt alloy; and synthetic resins including polyolefin resins such as polyvinyl chloride, polyethylene, polypropylene, or cyclic polyolefin, polystyrene resins, polymethylpentene resins such as poly-(4-methylpentene-1), polycarbonate resins, acrylic resins, ABS resins, polyester resins such as polyethylene terephthalate, or polyethylene naphthalate, and polyamide resins such as butadiene-styrene copolymer, nylon 6, nylon 6,6, nylon 6,10, or nylon 12. These materials may be used alone, or two or more of them may be used in combination. It is provided that the material constituting the projecting portion 22 of one or more embodiments may be the same as the material constituting the wing 21. That is, in one or more embodiments it may be provided that the material constituting the projecting portion 22 is the same as the materials constituting the balloon 10 and the wing 21. Due to such configuration of the projecting portion 22, the joint strength between the wing 21 and the projecting portion 22 can be increased. Further, the wing 21 and the projecting portion 22 are integrated in one or more embodiments, which will be described later. When the wing 21 and the projecting portion 22 are configured as described above, the joint strength between the wing 21 and the projecting portion 22 can be increased, whereby the strength of the balloon 10 can be increased.

In one or more embodiments, the Shore hardness of the projecting portion 22 is 30 D or more and 80 D or less, and the Rockwell hardness of the projecting portion 22 is 50 or more and 150 or less. When being configured as described above, the projecting portion 22 can easily catch on the stenosed part. When a resin having the hardness as described above is selected from the abovementioned materials, the projecting portion 22 can be formed to have a predetermined hardness.

As shown in FIG. 6, in one or more embodiments it is provided that, in a cross section perpendicular to the long axis direction of the balloon 10, a direction which is an extending direction of the wing 21 and which is from the base first end part 22a1 toward the tip part 21b of the wing 21 has a one-circumferential-direction component with respect to the long axis of the balloon 10, and a direction which is from the base first end part 22a1 toward the tip part 22b of the projecting portion 22 has an other-circumferential-direction component with respect to the long axis of the balloon 10. That is, in one or more embodiments it is provided that the direction from the base first end part 22a1 toward the tip part 22b has a component in the direction from the tip part 21b of the wing 21 toward the base first end part 22a1. In other words, a linear component passing through the base first end part 22a1 and the base second end part 22a2 in a vector from the base first end part 22a1 of the projecting portion 22 toward the tip part 21b of the wing 21 having the projecting portion 22, and a linear component passing through the base first end part 22a1 and the base second end part 22a2 in a vector from the base first end part 22a1 of the projecting portion 22 toward the tip part 22b of the projecting portion 22 are opposite. Due to such configuration of the projecting portion 22, the projecting portion 22 is less likely to interfere with the inner wall of the blood vessel when the balloon 10 passes through the blood vessel, whereby the passage of the balloon 10 within the blood vessel can be improved.

In one or more embodiments, the projecting portion 22 is exposed when the wing 21 is wrapping. That is, in one or more embodiments it is provided that the projecting portion 22 is at a position where the wings 21 do not overlap each other when the wings 21 are wrapping. Due to such configuration of the projecting portion 22, when the balloon 10 is inflated at the stenosed part, the projecting portion 22 easily catches on the stenosed part in the middle of the inflation of the balloon 10. Thus, the balloon 10 is easily fixed to the stenosed part, whereby the stenosed part can be easily dilated.

Particularly, in one or more embodiments the projecting portion 22 is provided at a location exposed on the outermost surface in a wrapping state and closer to the tip part 21b of the wing 21 in an area from the tip part 21b to the root part of the wing 21. Due to such configuration of the projecting portion 22, the projecting portion 22 easily catches on the stenosed part in an initial stage of the inflation of the balloon 10. Further, due to the presence of the projecting portion 22 at the tip part 21b of the wing 21, when the inflated balloon 10 is again deflated, the balloon 10 easily returns to the state, the same as the state before inflation, where the wing 21 is wrapping. Thus, even when the balloon 10 is inserted into the blood vessel again, the balloon 10 can satisfactorily pass through the blood vessel.

In one or more embodiments, the number of the projecting portions 22 is two or more, and three or more. Due to the lower limit value of the number of the projecting portions 22 being set as described above, the balloon 10 can be reliably fixed to the stenosed part. Further, in one or more embodiments the number of the projecting portions 22 is five or less, and four or less. Due to the upper limit value of the number of the projecting portions 22 being set as described above, the passage of the balloon 10 within the blood vessel can be enhanced. In one or more embodiments, the number of the projecting portions 22 is the same as the number of the wings 21. In one or more embodiments, each of the wings 21 are provided with one projecting portion 22. However, each of the wings 21 may be provided with a plurality of projecting portions 22. When each of the wings 21 is provided with a plurality of projecting portions 22, the projecting portions 22 may be provided adjacent to each other or separated from each other.

In one or more embodiments, it is provided that at least one projecting portion 22 is on each of the plurality of wings 21. Due to such configuration of the projecting portion 22, the balloon 10 can be firmly fixed to the stenosed part, whereby the stenosed part can be efficiently dilated.

In one or more embodiments, it is provided that the number of the projecting portions 22 is equal to the number of the wings 21, and each of the wings 21 is provided with one projecting portion 22. Particularly, in one or more embodiments it is provided that the number of the wings 21 is two or more and five or less, the number of the projecting portions 22 is equal to the number of the wings 21, and each of the wings 21 is provided with one projecting portion 22. Due to such configuration of the projecting portion 22, it is possible to achieve both improvement in passage of the balloon 10 within the blood vessel and dilation force for the stenosed part.

As shown in FIG. 6, in one or more embodiments it is provided that, in a cross section perpendicular to the long axis direction of the balloon 10, a height L1 from the base 22a of the projecting portion 22 to the tip 22b of the projecting portion 22 may be greater than a length L2 of the base 22a of the projecting portion 22. The length L2 indicates the length of the base 22a of the projecting portion 22 in the wrapping direction of the wing 21. That is, in one or more embodiments in a cross section perpendicular to the long axis direction of the balloon 10, a height is provided from a straight line X1 passing through the base first end part 22a1 and the base second end part 22a2 to a tip 22b of the projecting portion 22 may be greater than a distance from the base first end part 22a1 to the base second end part 22a2. Due to such configuration of the projecting portion 22, the projecting portion 22 easily catches on the stenosed part, whereby the stenosed part is easily dilated. When the length of the base 22a is increased, that is, when the base 22a is thick, the projecting portion 22 is less likely to collapse, which is effective for dilating the stenosed part.

In one or more embodiments, the height of the projecting portion 22 is 0.03 mm or more, 0.05 mm or more, and 0.10 mm or more. Due to the lower limit value of the height of the projecting portion 22 being set as described above, the projecting portion 22 is easily fixed to the stenosed part, whereby the stenosed part is easily dilated. Further, in one or more embodiments the height of the projecting portion 22 is 1.00 mm or less, 0.80 mm or less, and 0.65 mm or less. Due to the upper limit value of the height of the projecting portion 22 being set as described above, the passage of the balloon 10 within the blood vessel can be improved. Note that the height of the projecting portion 22 refers to the height L1 from the base 22a of the projecting portion 22 to the tip 22b of the projecting portion 22.

In one or more embodiments, the length of the base 22a of the projecting portion 22 is 0.01 mm or more, 0.03 mm or more, and 0.05 mm or more. Due to the lower limit value of the length of the base 22a of the projecting portion 22 being set as described above, the projecting portion 22 can be easily hooked and fixed on the stenosed part, whereby the stenosed part is easily dilated. Further, in one or more embodiments the length of the base 22a of the projecting portion 22 is 1.20 mm or less, 1.00 mm or less, and 0.85 mm or less. Due to the upper limit value of the length of the base 22a of the projecting portion 22 being set as described above, the projecting portion 22 is less likely to interfere with the inner wall of the blood vessel while the balloon 10 passes through the blood vessel. The length of the base part 22a of the projecting portion 22 refers to the length L2 from a base first end part 22a1 to a second end 22a2 of the base 22a of the projecting portion 22.

In one or more embodiments it is also provided that, in a cross section perpendicular to the long axis direction of the balloon 10, the height L1 from the base 22a of the projecting portion 22 to the tip 22b of the projecting portion 22 is less than the length L2 of the base 22a of the projecting portion 22. That is, in one or more embodiments it is also provided that in cross section perpendicular to the long axis direction of the balloon 10, a height from a straight line X1 passing through the base first end part 22a1 and the base second end part 22a2 to a tip 22b of the projecting portion 22 is less than a distance from the base first end part 22a1 to the base second end part 22a2. Such configuration of the projecting portion 22 can provide an effect of making the projecting portion 22 easily catch on the stenosed part in the middle of inflation of the balloon 10 and an effect of improving passage of the balloon 10 within the blood vessel.

As shown in FIGS. 7 and 8, in one or more embodiments it is provided that the projecting portion 22 is at least partially provided with the discontinuous part 23 in the distal and proximal direction of the shaft 2. Due to such configuration of the projecting portion 22, the projecting portion 22 can be made flexible and less likely to interfere with the inner wall of the blood vessel while the balloon 10 passes through the blood vessel.

The discontinuous part 23 may have a depth from the tip 22b of the projecting portion 22 to the base 22a of the projecting portion 22, or may have a depth from the tip 22b of the projecting portion 22 to the middle between the tip 22b of the projecting portion 22 and the base 22a of the projecting portion 22. That is, the discontinuous part 23 may exist throughout the height of the projecting portion 22 or may exist up to the middle of the projecting portion 22 in the height direction. In one or more embodiments it is provided that the discontinuous part 23 has a depth from the tip 22b of the projecting portion 22 to the base 22a of the projecting portion 22. Due to such configuration of the discontinuous part 23, the flexibility of the projecting portion 22 can be increased.

In one or more embodiments, the number of the discontinuous part 23 may be one, but it is provided to be two or more. Due to such configuration of the discontinuous part 23, the projecting portion 22 becomes more flexible.

In one or more embodiments, the length of the discontinuous part 23 in the distal and proximal direction is 0.03 mm or more, 0.05 mm or more, and 0.10 mm or more. Due to the lower limit value of the length of the discontinuous part 23 in the distal and proximal direction being set as described above, the projecting portion 22 can be made more flexible. Further, in one or more embodiments the length of the discontinuous part 23 in the distal and proximal direction is 1.00 mm or less, 0.80 mm or less, and 0.65 mm or less. Due to the upper limit value of the length of the discontinuous part 23 in the distal and proximal direction being set as described above, flexibility and rigidity of the projecting portion 22 can be balanced, whereby the projecting portion 22 can reliably catch on the stenosed part.

In one or more embodiments, the total length of the discontinuous parts 23 in the distal and proximal direction is shorter than the total length of the projecting portion 22 in the distal and proximal direction. Due to such configuration of the projecting portion 22, the projecting portion 22 becomes flexible, which improves passage of the balloon 10 within the blood vessel. Further, the projecting portion 22 has rigidity enough to catch on the stenosed part, whereby the balloon 10 catches on the stenosed part and can sufficiently dilate the stenosed part.

In one or more embodiments, the projecting portion 22 is formed with a plurality of holes 24 aligned in the distal and proximal direction of the shaft 2. Due to such configuration of the projecting portion 22, the flexibility of the projecting portion 22 is increased, so that the projecting portion 22 easily bends in the circumferential direction of the balloon 10. Thus, the projecting portion 22 is less likely to catch on the inner wall of the blood vessel when the balloon 10 passes through the blood vessel.

The shape of each hole 24 is not particularly limited, and may be a circle, an ellipse, a polygon, or the like. Among these, a circle or an ellipse is provided in one or more embodiments. Due to such configuration of the holes 24, when stress is applied to the projecting portion 22, damage of the projecting portion 22 such as rupture of the projecting portion 22 from the holes 24 can be prevented.

In one or more embodiments, the length of each hole 24 in the long axis direction is shorter than the length L1 from the tip part 22*b* of the projecting portion 22 to the base part 22*a* of the projecting portion 22. That is, in one or more embodiments the length of the hole 24 in the long axis direction is shorter than the height of the projecting portion 22. Due to such configuration of the holes 24, the projecting portion 22 becomes adequately rigid, so that the projecting portion can easily catch on the stenosed part.

In addition, it is also provided in one or more embodiments that a recess 25 extending along the distal and proximal direction of the shaft 2 is formed in the projecting portion 22. The recess 25 is, for example, a groove or a hole-shaped dent that does not penetrate. Due to such configuration of the projecting portion 22, the projecting portion 22 becomes flexible and is less likely to catch on the inner wall of the blood vessel when the balloon 10 passes through the blood vessel.

It is also provided in one or more embodiments that the projecting portion 22 has both a plurality of holes 24 and the recess 25 formed therein. Due to such configuration of the projecting portion 22, the flexibility of the projecting portion 22 can be further increased, whereby the passage of the balloon 10 within the blood vessel can be further improved.

It is provided in one or more embodiments that, in a cross section perpendicular to the long axis direction of the balloon 10, the projecting portion 22 has an arc 26 that protrudes toward the tip part 21*b* of the wing 21. In other words, it is provided in one or more embodiments that, in the projecting portion 22, at least one of the surfaces along the long axis direction of the balloon 10 is a curved surface protruding toward the tip 21*b* of the wing 21. Due to such configuration of the projecting portion 22, the projecting portion 22 easily catches on the stenosed part even in the middle of the inflation of the balloon 10, whereby the stenosed part can be more efficiently dilated.

It is provided in one or more embodiments that, in a cross section perpendicular to the long axis direction of the balloon 10, the projecting portion 22 has the arc 26 on a side opposite to the tip 21*b* of the wing 21. Due to such configuration of the projecting portion 22, the projecting portion 22 can easily catch on the stenosed part.

In one or more embodiments, it is provided that, in cross section perpendicular to the long axis direction of the balloon 10, the projecting portion 22 has an arc at least at a part from the base first end part 22*a*1 to the tip 22*b* of the projecting portion 22 and at least at a part from the base second end part 22*a*2 to the tip 22*b* of the projecting portion 22. Due to such configuration of the projecting portion 22, increase the rigidity of the projecting portion 22, the projecting portion 22 can easily catch on the stenosed part.

In one or more embodiments, it is provided that, in cross section perpendicular to the long axis direction of the balloon 10, the projecting portion 22 has a first arc from the base first end part 22*a*1 to the tip 22*b* of the projecting portion 22 and a second arc from the base second end part 22*a*2 to the tip 22*b* of the projecting portion 22, the first arc and the second arc are convex in the same direction, and the length of the first arc is shorter than the length of the second arc. Due to such configuration of the projecting portion 22, the projecting portion 22 can easily catch on the stenosed part.

It is provided in one or more embodiments that, in a cross section perpendicular to the long axis direction of the balloon 10, the base 22*a* of the projecting portion 22 includes a base first end part 22*a*1 farther from the tip 21*b* of the wing 21, and a base second end part 22*a*2 closer to the tip 21*b* of the wing 21, and with respect to the outer surface of the wing 21, a distance L3 from a point P1 where a perpendicular line X2 from the tip 22*b* of the projecting portion 22 to a straight line X1 passing through the base first end part 22*a*1 and the base second end part 22*a*2 is in contact with the outer surface of the wing 21 to the base first end part 22*a*1 is greater than a distance L2 from the base first end part 22*a*1 to the base second end part 22*a*2. That is, it is also provided in one or more embodiments that on the outer surface of the wing 21 in cross section perpendicular to the long axis direction of the balloon 10, a distance from a point of intersection where a perpendicular line X2 from the tip 22*b* of the projecting portion 22 to a straight line X1 passing through the base first end part 22*a*1 and the base second end part 22*a*2 contacts a straight line X1 passing through the base first end part 22*a*1 and the base second end part 22*a*2 to the base first end part 22*a*1 is greater than a distance L2 from the base first end part 22*a*1 to the base second end part 22*a*2. Due to such configuration of the projecting portion 22, the projecting portion 22 is less likely to interfere with the inner wall of the blood vessel while the balloon 10 passes through the blood vessel, whereby passage of the balloon 10 is improved. In addition, the projecting portion 22 easily catches on the stenosed part, whereby the stenosed part can be efficiently dilated. In addition, when the balloon 10 is rotated in the direction from the tip 21*b* of the wing 21 toward the projecting portion 22 while being placed in the stenosed part, the projecting portion 22 more easily catches on the stenosed part, whereby the stenosed part is more easily dilated.

In one or more embodiments, the distance L3 from the point P1 where the perpendicular line X2 from the tip 22*b* of the projecting portion 22 to the straight line X1 passing through the base first end part 22*a*1 and the base second end part 22*a*2 is in contact with the outer surface of the wing 21 to the base first end part 22*a*1 is 1.1 times or more, 1.2 times or more, and 1.3 times or more the distance L2 from the base first end part 22*a*1 to the second end part 22*a*2. Due to the lower limit value of the ratio between the distance L3 and the distance L2 being set as described above, the projecting portion 22 is less likely to interfere with the inner wall of the blood vessel while the balloon 10 passes through the blood vessel. Further, in one or more embodiments the distance L3 from the point P1 where the perpendicular line X2 from the tip 22*b* of the projecting portion 22 to the straight line X1 passing through the base first end part 22*a*1 and the base second end part 22*a*2 is in contact with the outer surface of the wing 21 to the base first end part 22*a*1 is 2.0 times or less, 1.8 times or less, and 1.5 times or less the distance L2 from the base first end part 22*a*1 to the base second end part 22*a*2. Due to the upper limit value of the ratio between the distance L3 and the distance L2 being set as described above, the projecting portion 22 can more easily catch on the stenosed part.

It is provided in one or more embodiments that, in a cross section perpendicular to the long axis direction of the balloon 10, the distance L3 from the point P1 where the perpendicular line X2 from the tip 22*b* of the projecting portion 22 to the straight line X1 passing through the base first end part 22*a*1 and the base second end part 22*a*2 is in contact with the outer surface of the wing 21 to the base first end part 22*a*1 is less than the height L1 from the base 22*a* of the projecting portion 22 to the tip 22*b* of the projecting portion 22. That is, it is provided in one or more embodiments that the distance L3 from the point P1 where the perpendicular line X2 from the tip 22*b* of the projecting portion 22 to the straight line X1 passing through the base first end part 22a1 and the base second end part 22a2 is in contact with the outer surface of the wing 21 to the base first end part 22a1 is greater than the distance L2 from the base first end part 22a1 to the base second end part 22a2 and less than the height L1 from the base 22a of the projecting portion 22 to the tip 22b of the projecting portion 22. Due to such configuration of the projecting portion 22, it is possible to improve both passage of the balloon 10 within the blood vessel and efficiency in dilating the stenosed part.

In one or more embodiments, the distance L3 from the point P1 where the perpendicular line X2 from the tip 22b of the projecting portion 22 to the straight line X1 passing through the base first end part 22a1 and the base second end part 22a2 is in contact with the outer surface of the wing 21 to the base first end part 22a1 is 0.03 mm or more, 0.05 mm or more, and 0.10 mm or more. Due to the lower limit value of the distance L3 being set as described above, the projecting portion 22 more easily catches on the stenosed part. Further, in one or more embodiments the distance L3 from the point P1 where the perpendicular line X2 from the tip 22b of the projecting portion 22 to the straight line X1 passing through the base first end part 22a1 and the base second end part 22a2 is in contact with the outer surface of the wing 21 to the base first end part 22a1 is 1.00 mm or less, 0.85 mm or less, and 0.65 mm or less. Due to the upper limit value of the distance L3 being set as described above, the projecting portion 22 is less likely to interfere with the inner wall of the blood vessel while the balloon 10 passes through the blood vessel, whereby passage of the balloon 10 can be improved.

In one or more embodiments, it is provided that, in a cross section perpendicular to the long axis direction of the balloon 10, the projecting portion 22 has two arcs 26 protruding toward the tip 21b of the wing 21. One of the two arcs connects the tip 22b of the projecting portion 22 and the base part 22a1 of the projecting portion 22, and the other connects the tip 22b of the projecting portion 22 and the base part 22a2 of the projecting portion 22. In other words, in one or more embodiments it is provided that, in the projecting portion 22, the two surfaces along the long axis direction of the balloon 10 are curved surfaces protruding toward the tip 21b of the wing 21. Due to such configuration of the projecting portion 22, the projecting portion 22 easily catches on the stenosed part.

A method for producing the balloon catheter according to one or more embodiments of the present disclosure includes: a step of preparing a resin block having a plurality of protrusions in a cross section perpendicular to the long axis direction, the protruding directions of the plurality of protrusions having a one-circumferential-direction component; a step of preparing a hollow mold; and a step of placing the resin block inside the mold.

As shown in FIG. 9, the balloon 10 is produced using a resin block 110 having a plurality of protrusions 111 in a cross section perpendicular to the long axis direction, the protruding directions of the plurality of protrusions 111 having a one-circumferential-direction component. The balloon 10 is produced by blow molding.

When the balloon 10 is produced, the resin block 110 having a plurality of protrusions 111 is prepared. A cylindrical resin block (parison) 110 is produced by extrusion molding. In a cross section perpendicular to the long axis direction, the protruding directions of the protrusions 111 have a one-circumferential-direction component. That is, in a cross section perpendicular to the long axis direction of the resin block 110, the protruding directions of the protrusions 111 are inclined in the same direction. Since the resin block 110 is configured as described above, the projecting portion 22 can be formed integrally with the balloon 10.

Before stretch blow molding is performed, a step may be added of stretching and extending the portion in the axial direction to become the proximal tapered portion 12 and the distal tapered portion 13 in the resin block 110 while locally heating the portion to be molded as the proximal tapered portion 12 and the distal tapered portion 13 of the balloon 10 shown in FIG. 3. Thus, the molded tapered portions 12 and 13 can be sufficiently reduced in thickness. In that case, the portion which has been reduced in thickness by stretching is cut while leaving a predetermined length, whereby a preformed resin block 110 is formed.

Meanwhile, a hollow mold is prepared. The mold may be hollow so that the resin block 110 can be placed therein. As shown in FIG. 10, the mold 120 has recessed parts 121 in which the protrusions 111 can be placed in one or more embodiments. Since the mold 120 has such a cavity, the tip part 22b of the projecting portion 22 can be sharpened, whereby the balloon 10 can easily catch on the stenosed part. The cavity of the mold 120 indicates the shape inside the mold 120.

A single mold 120 may be used, or a plurality of molds 120 may be used. It is provided in one or more embodiments to form the balloon 10 using a plurality of molds 120 by changing the shapes of the cavity of the mold 120 and the recessed parts 121 in a stepwise manner from the shape of the resin block 110 to the shape of the balloon 10. Due to such molding of the balloon 10, the mass production of the balloons 10 having small errors in shape and dimension is enabled.

Then, the resin block 110 is placed inside the mold 120. The resin block 110 is placed in the cavity of the mold 120. When the mold 120 has the recessed parts 121, the protrusions 111 are placed in the recessed parts 121. Then, the mold 120 is closed, and compressed air is supplied to the interior, by which the resin block 110 is expanded and molded into the cavity shape. The blow molding may be performed under heating conditions, and may be performed several times. Further, stretching in the radial direction and stretching in the long axis direction may be simultaneously performed, or after either of the stretching in the radial direction or the stretching in the long axis direction is performed, the other may be performed. Stretching and blowing may be performed at the same time, or after either of stretching or blowing is performed, the other may be performed. After blow molding, the compressed air is removed from the inside of the balloon 10. At this time, in one or more embodiments the balloon 10 is heat fixed in order to fix the folds and dimensions of the balloon 10 to improve foldability during rewrapping and to increase strength. Specifically, it is provided in one or more embodiments that the compressed air is removed from the inside of the balloon 10 with portions where the folds are to be formed being pressed or with a mold having a predetermined shape being in contact with the balloon.

In order to form the holes 24 or the recess 25 in the projecting portion 22 of the balloon 10, the recessed part 121 inside the mold 120 is configured to have a member that can form the recess 25, or the holes 24 and the recess 25 are formed in the projecting portion 22 of the balloon 10 after blow molding by post treatment, for example. After the balloon 10 is molded, the holes 24 can be formed in the projecting portion 22 by laser processing or punching. In particular, it is provided in one or more embodiments to form the holes 24 and the recess 25 in the projecting portion 22 by using a configuration in which the recessed part 121 includes a member that can form the holes 24 and the recess 25. By adopting such a method, it is possible to produce the balloon 10 with a small error in position, shape, and dimensions of the holes 24 and the recess 25 in a short time.

As described above, the balloon catheter according to one or more embodiments of the present disclosure includes: a shaft having a distal side and a proximal side; and a balloon provided at the distal side of the shaft, wherein the balloon has a plurality of wings in a deflated state, the each wing has a projecting portion on an outer surface in a wrapping state, and a projecting direction of which is opposite to the wrapping direction of the wing, in cross section perpendicular to a long axis direction of the balloon, a base of the projecting portion has a base first end part farther from a tip of the wing and a base second end part closer to the tip of the wing, and a tip of the projecting portion is closer to a base of the wing respect to a line passing through the base first end part which is perpendicular to a line passing through the base first end part and the base second end part. With such a configuration, passage of the balloon within a blood vessel can be improved. Further, the balloon can easily catch on the stenosed part, and a strong stress is applied to the stenosed part, whereby the stenosed part can be sufficiently dilated.

The present application claims the benefit of priority based on Japanese patent application number 2017-230943 filed on Nov. 30, 2017. The entire content of the specification of Japanese patent application number 2017-230943 filed on Nov. 30, 2017 is incorporated herein by reference.

DESCRIPTION OF REFERENCE SIGNS

1: balloon catheter
2: shaft
3: inner tube
4: outer tube
5: hub
6: fluid injection portion
7: guide wire insertion portion
10: balloon
11: straight tube portion
12: proximal tapered portion
13: distal tapered portion
14: proximal sleeve
15: distal sleeve
21: wing
21b: tip part of wing
22: projecting portion (projection)
22a: base of projecting portion
22a1: base first end part
22a2: base second end part
22b: tip of projecting portion
23: discontinuous part
24: hole
25: recess
26: arc
110: resin block
111: protrusion
120: mold
121: recessed part
X1: straight line passing through base first end part and base second end part
X2: perpendicular line from tip of projecting portion to straight line X1
P1: point where perpendicular line X2 and outer surface of wing contact L1: height from base of projecting portion to tip of projecting portion
L2: length of base of projecting portion (distance from base first end part to base second end part)
L3: distance from point P1 to base first end part Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

The invention claimed is:

1. A balloon catheter comprising:
a shaft having a distal side and a proximal side; and
a balloon provided at the distal side of the shaft,
wherein:
  the balloon has a plurality of wings in a deflated state,
  each of the wings has a projection on an outer surface in a wrapped state, and
  each of the projections has a projecting direction, which is opposite to a wrapping direction of the wing,
  in a cross section that is perpendicular to a long axis direction of the balloon, a base of the projection has a base first end part farther from a tip of the wing and a base second end part closer to the tip of the wing,
  a tip of the projection is closer to a base of the wing with respect to a line passing through the base first end part which is perpendicular to a line passing through the base first end part and the base second end part,
  the line passing through the base first end part which is perpendicular to the line passing through the base first end part and the base second end part as a boundary line, the base second end part is located on a side of the boundary line where the tip of the wing exists, and
  the line passing through the base first end part which is perpendicular to the line passing through the base first end part and the base second end part as a boundary line, the tip of the projection is located on a side of the boundary line where the base second end part does not exist.

2. The balloon catheter according to claim 1, wherein, in the cross section that is perpendicular to the long axis direction of the balloon, a linear component passing through the base first end part and the base second end part in a vector from the base first end part of the projection toward the tip of the wing having the projection, and a linear component passing through the base first end part and the base second end part in a vector from the base first end part of the projection toward the tip of the projection are opposite.

3. The balloon catheter according to claim 1, wherein the projection is exposed when the wings are wrapping.

4. The balloon catheter according to claim 1, wherein the plurality of wings comprises at least two wings, and the balloon catheter contains the projections in a number of two or more and five or less.

5. The balloon catheter according to claim 1, wherein at least one projection is provided on each of the plurality of wings.

6. The balloon catheter according to claim 1,
wherein the projection is at least partially provided with a discontinuous part in a distal and proximal direction of the shaft.

7. The balloon catheter according to claim 1,
wherein the projection is formed with a plurality of holes aligned in a distal and proximal direction of the shaft.

8. The balloon catheter according to claim 1,
wherein the projection is formed with a recess extending along a distal and proximal direction of the shaft.

9. The balloon catheter according to claim 1,
wherein, in the cross section that is perpendicular to the long axis direction of the balloon, a height from a straight line passing through the base first end part and the base second end part to a tip of the projection is greater than a distance from the base first end part to the base second end part.

10. The balloon catheter according to claim 1,
wherein, in the cross section that is perpendicular to the long axis direction of the balloon, a height from a straight line passing through the base first end part and the base second end part to a tip of the projection is less than a distance from the base first end part to the base second end part.

11. The balloon catheter according to claim 1,
wherein, in the cross section that is perpendicular to the long axis direction of the balloon, the projection has an arc at least at a part from the base first end part to the tip of the projection and at least at a part from the base second end part to the tip of the projection.

12. The balloon catheter according to claim 1,
wherein, on the outer surface of the wing in the cross section that is perpendicular to the long axis direction of the balloon,
a distance from a point of intersection where a perpendicular line from the tip of the projection to a straight line passing through the base first end part and the base second end part contacts a straight line passing through the base first end part and the base second end part to the base first end part is greater than a distance from the base first end part to the base second end part.

13. The balloon catheter according to claim 1,
wherein a material constituting the projection is the same as a material constituting the wings.

14. A method for producing a balloon catheter, the method comprising:
preparing a resin block having a plurality of protrusions in a cross section that is perpendicular to a long axis direction, each of the plurality of protrusions having a protrusion direction that has a one-circumferential-direction component;
preparing a hollow mold; and
placing the resin block inside the mold,
wherein the balloon catheter comprises:
a shaft having a distal side and a proximal side; and
a balloon provided at the distal side of the shaft,
wherein:
the balloon has a plurality of wings in a deflated state,
each of the wings has a projection on an outer surface in a wrapped state, and
each of the projections has a projecting direction, which is opposite to a wrapping direction of the wing,
in a cross section that is perpendicular to a long axis direction of the balloon, a base of the projection has a base first end part farther from a tip of the wing and a base second end part closer to the tip of the wing,
a tip of the projection is closer to a base of the wing with respect to a line passing through the base first end part which is perpendicular to a line passing through the base first end part and the base second end part,
the line passing through the base first end part which is perpendicular to the line passing through the base first end part and the base second end part as a boundary line, the base second end part is located on a side of the boundary line where the tip of the wing exists, and
the line passing through the base first end part which is perpendicular to the line passing through the base first end part and the base second end part as a boundary line, the tip of the projection is located on a side of the boundary line where the base second end part does not exist.

15. The method for producing a balloon catheter according to claim 14,
wherein the mold has a recessed part in which the protrusions are placeable.

16. The balloon catheter according to claim 1,
wherein the projection is configured such that an angle between a straight line connecting the base first end part of the projection and the tip of the projection and a straight line connecting the base first end part of the projection and the tip of the wing exceeds 90 degrees.

17. The balloon catheter according to claim 1,
wherein in the cross section perpendicular to the long axis direction of the balloon, the projection has arcs protruding toward the tip of the wing from the base first end part to the tip of the projection and from the base second end part to the tip of the projection.

* * * * *